US010605875B2

(12) United States Patent
Bailey

(10) Patent No.: US 10,605,875 B2
(45) Date of Patent: Mar. 31, 2020

(54) CONTRAST SYSTEM AND METHODS FOR REFLECTIVE MARKERS

(71) Applicant: Brent Andrew Bailey, Toronto (CA)

(72) Inventor: Brent Andrew Bailey, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 61 days.

(21) Appl. No.: 15/688,134

(22) Filed: Aug. 28, 2017

(65) Prior Publication Data
US 2019/0064290 A1 Feb. 28, 2019

(51) Int. Cl.
| | | |
|---|---|---|
| *G06K 9/00* | (2006.01) | |
| *G01R 33/28* | (2006.01) | |
| *G01R 33/56* | (2006.01) | |
| *A61B 34/00* | (2016.01) | |
| *A61B 90/00* | (2016.01) | |
| *A61B 34/20* | (2016.01) | |
| *G01R 33/58* | (2006.01) | |

(52) U.S. Cl.
CPC ............ *G01R 33/287* (2013.01); *A61B 34/25* (2016.02); *A61B 90/36* (2016.02); *A61B 90/39* (2016.02); *G01R 33/56* (2013.01); *A61B 2034/2051* (2016.02); *A61B 2034/2055* (2016.02); *A61B 2090/3983* (2016.02); *G01R 33/283* (2013.01); *G01R 33/58* (2013.01)

(58) Field of Classification Search
CPC . A61B 34/20; A61B 34/10; A61B 2090/3983; A61B 2090/373
See application file for complete search history.

(56) References Cited

U.S. PATENT DOCUMENTS

| | | | |
|---|---|---|---|
| 6,978,167 B2 | 12/2005 | Dekel et al. | |
| 7,945,311 B2 | 5/2011 | McCloy et al. | |
| 8,672,490 B2 | 3/2014 | Shafer et al. | |
| 9,526,587 B2 | 12/2016 | Zhao et al. | |
| 2004/0002642 A1* | 1/2004 | Dekel | G06K 9/3216 600/407 |
| 2007/0239169 A1 | 10/2007 | Plaskos et al. | |
| 2010/0168562 A1* | 7/2010 | Zhao | A61B 34/30 600/426 |

(Continued)

*Primary Examiner* — Vu Le
*Assistant Examiner* — Guillermo M Rivera-Martinez
(74) *Attorney, Agent, or Firm* — Rowand LLP

(57) ABSTRACT

A contrast system and methods for improving optical detection during a medical procedure, the system involving: a tracking marker, each tracking marker comprising a tracking marker coupling feature; and a contrast element, each contrast element comprising a contrast element coupling feature and an optically non-reflective feature, the contrast element coupling feature configured to complement the tracking marker coupling feature, each contrast element configured to respectively accommodate, by backing, each tracking marker, and contrast element configured to respectively facilitate coupling each tracking marker with a trackable object through a background object via at least one of a contrast element fastening feature and a trackable object fastening feature, whereby at least one of optical contrast and imaging in relation to the tracking marker and the background object is enhanced, false detection of the tracking marker is minimized, and optical detection of the tracking marker is improved.

20 Claims, 5 Drawing Sheets

(56) References Cited

U.S. PATENT DOCUMENTS

| | | | | |
|---|---|---|---|---|
| 2011/0098553 A1* | 4/2011 | Robbins | ............... | A61B 5/055 |
| | | | | 600/410 |
| 2013/0135734 A1* | 5/2013 | Shafer | ............... | B65D 75/327 |
| | | | | 359/544 |
| 2013/0345718 A1* | 12/2013 | Crawford | ............ | A61B 17/025 |
| | | | | 606/130 |
| 2015/0018622 A1* | 1/2015 | Tesar | ................. | A61B 1/05 |
| | | | | 600/202 |
| 2015/0038836 A1* | 2/2015 | Hladio | ............... | A61B 5/4571 |
| | | | | 600/424 |
| 2016/0256225 A1* | 9/2016 | Crawford | ............... | A61B 34/20 |
| 2017/0258526 A1* | 9/2017 | Lang | ................ | H05K 999/99 |
| 2017/0258535 A1* | 9/2017 | Crawford | ............... | A61B 34/20 |
| 2018/0071029 A1* | 3/2018 | Srimohanarajah | ..... | A61B 46/10 |
| 2018/0325610 A1* | 11/2018 | Cameron | | |

\* cited by examiner

CONTRAST SYSTEM AND METHODS FOR REFLECTIVE MARKERS

TECHNICAL FIELD

Generally, the present disclosure technically relates to tracking marker systems and methods. More particularly, the present disclosure technically relates to passive tracking marker systems and methods. Even more particularly, the present disclosure technically relates to enhancing passive tracking marker systems and methods.

BACKGROUND

In the related art, a tracking system (or navigation system) uses many passive tracking markers that are arranged in a three-dimensional (3D) geometric pattern around a cylinder or similar large shape, wherein a tracking camera attempts to image all the many tracking markers. However, the related art has experienced erroneous tracking as the tracking camera frequently images an excess number of tracking markers than are actually disposed in the 3D geometric pattern. As such, a potential exists for the tracking software to lose its ability to accurately track the actual number of markers. In these related art cases, an excessive number of tracking markers is necessary to compensate for the tracking error to track an object, notwithstanding the object's orientation in a 3D space, e.g., to acquire a visibility of 360 degrees around the object.

Referring to related art FIGS. 1A and 1B, this related art problem exists with tracking systems having an end-effector, wherein the object being tracked is large enough, such that, when rotated, some tracking markers 5, e.g., spheres, are always hidden in relation to a stationary tracking camera (FIG. 1A), and wherein the object is thin enough, such that, in certain orientations, the tracking system observes an excess number of tracking markers 5, e.g., in an image showing markers 5' (FIG. 1B), thereby confusing the tracking algorithm. For example, a potential partial eclipse condition may occur; and the tracking algorithm also becomes confused as to a marker placement. This related art problem is especially problematic in relation to line-of-sight or "sight-line" when the tracking markers partially overlap with one another, thereby forming shapes which, when observed by a tracking camera, such as an infrared (IR) camera, the tracking markers are no longer recognized as their true shapes (FIG. 1B).

These related art systems and methods have experienced many challenges, including necessitating an excessive number of tracking markers to compensate for the tracking error as well as the erroneous observation as to the number and shapes of the tracking markers, thereby confusing the tracking algorithm. Therefore, a need exists for a system and methods that enhance tracking of the tracking markers.

SUMMARY

In addressing at least many of the challenges experienced in the related art, a contrast system and methods are described by the present disclosure which eliminates the use of an excessive number of compensatory tracking markers and minimizes erroneous observation as to the number and shapes of the tracking markers, thereby eliminating confusion by a tracking algorithm, and thereby providing reliable tracking data. In some embodiments of the present disclosure, the tracking markers are disposed outside of a drape, e.g., a surgical drape, and configured to couple with a trackable object, such as an end effector of a drive system, e.g., a robotic arm. Such configurations may effect at least one benefit of an enhancement of optical contrast, an elimination of optical occlusion, and integrability of the tracking markers integrated in relation to the drape.

In accordance with an embodiment of the present disclosure, a contrast system for improving optical detection during a medical procedure, the system comprising: at least one tracking marker, each at least one tracking marker comprising a tracking marker coupling feature; and at least one contrast element, each at least one contrast element comprising a contrast element coupling feature and an optically non-reflective feature, the contrast element coupling feature configured to complement the tracking marker coupling feature, each at least one contrast element configured to respectively accommodate, by backing, each at least one tracking marker, and each at least one contrast element configured to respectively facilitate coupling each at least one tracking marker with at least one trackable object through at least one background object via at least one of a contrast element fastening feature and a trackable object fastening feature, whereby at least one of optical contrast and imaging in relation to the at least one tracking marker and the at least one background object is enhanceable, false detection of the at least one tracking marker is minimizable, and optical detection of the at least one tracking marker is improvable.

In accordance with an embodiment of the present disclosure, a method of fabricating a contrast system for improving optical detection during a medical procedure comprises: providing at least one tracking marker, providing the at least one tracking marker comprising providing a tracking marker coupling feature for each at least one tracking marker; and providing at least one contrast element, providing the at least one contrast element comprising providing a contrast element coupling feature and an optically non-reflective feature for each at least one contrast element comprising, providing the contrast element coupling feature comprising configuring the contrast element coupling feature to complement the tracking marker coupling feature, and providing the at least one contrast element comprising: configuring each at least one contrast element to respectively accommodate, by backing, each at least one tracking marker, and configuring each at least one contrast element to respectively facilitate coupling each at least one tracking marker with at least one trackable object through at least one background object via a fastening feature, whereby optical contrast between that least one tracking marker and the at least one background object is enhanceable, false detection of the at least one tracking marker is minimizable, and optical detection of the at least one tracking marker is improvable.

In accordance with an embodiment of the present disclosure, a method of fabricating a contrast system for improving optical detection during a medical procedure, the method comprising: providing at least one tracking marker, providing the at least one tracking marker comprising providing a tracking marker coupling feature for each at least one tracking marker; and providing at least one contrast element, providing the at least one contrast element comprising providing a contrast element coupling feature and an optically non-reflective feature for each at least one contrast element comprising, providing the contrast element coupling feature comprising configuring the contrast element coupling feature to complement the tracking marker coupling feature, and providing the at least one contrast element comprising: configuring each at least one contrast element to respectively accommodate, by backing, each at least one tracking marker, and configuring each at least one contrast element to respectively facilitate coupling each at least one tracking marker with at least one trackable object through at least one background object via at least one of a contrast element fastening feature and a trackable object fastening feature, whereby at least one of optical contrast and imaging in relation to the at least one tracking marker and the at least one background object is enhanceable, false detection of the at least one tracking marker is minimizable, and optical detection of the at least one tracking marker is improvable.

Some of the features in the present disclosure are broadly outlined in order that the section, entitled Detailed Description, is better understood and that the present contribution to the art by the present disclosure is better appreciated. Additional features of the present disclosure are described hereinafter. In this respect, understood is that the present disclosure is not limited in its implementation to the details of the components or steps as set forth herein or as illustrated in the several figures of the Drawing, but are capable of being carried out in various ways which are also encompassed by the present disclosure. Also, understood is that the phraseology and terminology employed herein are for illustrative purposes in the description and are not regarded as limiting.

BRIEF DESCRIPTION OF THE DRAWING

The above, and other, aspects, and features, of the several embodiments in the present disclosure will be more apparent from the following Detailed Description as presented in conjunction with the following several figures of the Drawing.

Figure 1A:
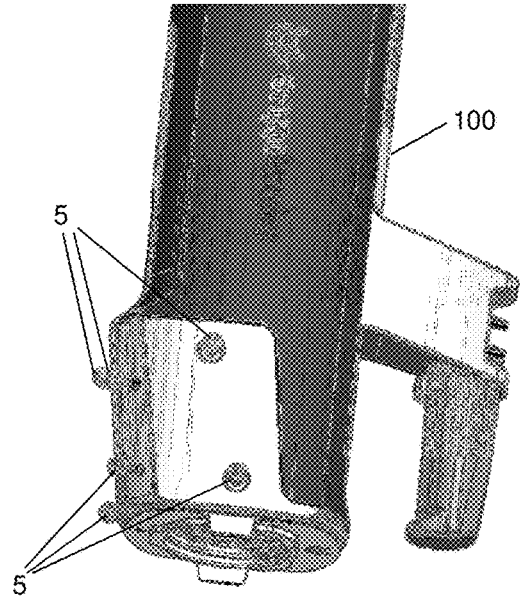
FIG. 1A is a diagram illustrating a perspective view of a plurality of tracking markers, as observed by a tracking camera of a tracking system, wherein an erroneous excess number and erroneous shapes of the tracking markers are observed, in accordance with the related art.

Corresponding reference numerals or characters indicate corresponding components throughout the several figures of the Drawing. Elements in the several figures are illustrated for simplicity and clarity and have not necessarily been drawn to scale. For example, the dimensions of some elements in the figures are emphasized relative to other elements for facilitating understanding of the various presently disclosed embodiments. Also, well-understood elements that are useful or necessary in commercially feasible embodiment are often not depicted to facilitate a less obstructed view of these various embodiments of the present disclosure.

DETAILED DESCRIPTION

The systems and methods described herein are useful in the field of imaging and tracking, such as used in relation to neurosurgery, including oncological care, neurodegenerative disease, stroke, brain trauma, and orthopedic surgery. The subject matter of the present disclosure is applicable to imaging and tracking in relation to other conditions or fields of medicine. Noted is that, while the present disclosure describes examples in the context of imaging and tracking in relation to neurosurgery, the subject matter of the present disclosure is applicable to other surgical procedures that may use imaging, such as MRI.

Various example apparatuses or processes are below-described. No below-described example embodiment limits any claimed embodiment; and any claimed embodiments may cover processes, products of manufacture, compositions of matter, devices, systems, or apparatuses that differ from those examples described below. The claimed embodiments are not limited to apparatuses or processes having all the features of any one of the processes, products of manufacture, compositions of matter, devices, systems, or apparatuses below-described or to features common to multiple or all the processes, products of manufacture, compositions of matter, devices, systems, or apparatuses below-described. The claimed embodiments optionally comprise any of the below described processes, products of manufacture, compositions of matter, devices, systems, or apparatuses.

Furthermore, numerous specific details are set forth in order to provide a thorough understanding of the disclosure. However, understood is that the embodiments described herein are practiced without these specific details. In other instances, well-known methods, procedures and components have not been described in detail so as not to obscure the embodiments described herein.

As used herein, the terms, "comprises" and "comprising" are to be construed as being inclusive and open ended, and not exclusive. Specifically, when used in the specification and claims, the terms, "comprises" and "comprising" and variations thereof denote the specified features, steps, or components that are included. These terms are not to be interpreted to exclude the presence of other features, steps or components.

As used herein, the term "exemplary" or "example" denotes "serving as an example, instance, or illustration," and should not be construed as preferred or advantageous over other configurations disclosed herein.

As used herein, the terms "about," "approximately," and "substantially" are intended to cover variations that may exist in the upper and lower limits of the ranges of values, such as variations in properties, parameters, and dimensions. In one non-limiting example, the terms "about," "approximately," and "substantially" are understood to denote plus or minus 20 percent or less than a described value.

Unless defined otherwise, all technical and scientific terms used herein are intended to have the same meaning as understood by one of ordinary skill in the art. Unless otherwise indicated, such as through context, as used herein, the following technical and scientific terms are intended to have the meanings as understood by one of ordinary skill in the art.

In embodiments of the present disclosure, the subject matter of the present disclosure generally involves a contrast system comprising contrast elements, such as dishes, the contrast elements comprising a non-reflective material, such as a nonreflective polymeric material, e.g., a nonreflective plastic, disposed behind the tracking markers, such as reflective or retroreflective markers, whereby contrast between the tracking markers and a background object, such as a plastic medical or surgical drape, covering a trackable object, e.g., an end-effector of a drive system, such as the Synaptive® Modus V™ system, is improvable, and whereby tracking is enhanceable. The contrast elements, e.g., the dishes, do not reflect a significant amount of light, e.g., IR light, back to a tracking camera. For at least this reason, the tracking markers more clearly "stand out" via optical contrast and are more clearly identifiable by the tracking camera.

Further, the subject matter of the present disclosure involves contrast elements, comprising dishes that have large dish heads which are configured to block a line-of-sight to tracking markers, e.g., tracking spheres, from being viewed at certain angles, e.g., wherein the tracking markers face away from the tracking camera, at which orientation the tracking markers are not intended to be observed by the tracking camera. By using these contrast elements, the number of "false" markers that would otherwise be perceived by related art tracking cameras is reduced in the embodiments of the present disclosure, whereby tracking reliability is improved, lost tracking data and confused errors are reduced, and the need for a more complex algorithm is reduced.

Still further, at least one of the tracking markers and the contrast elements are disposable as a consumable item or a biodegradable item. Alternatively, the contrast elements and/or the tracking markers may be integrally formed with a drape. At least one of the tracking markers and contrast elements are disposable as a consumable item or a biodegradable item in relation to a background object, such as a medical or surgical drape, if integrally formed therewith, for providing enhanced visibility to a tracking camera of a tracking system. The consumable feature provides an alternative to reusable tracking markers which otherwise tend degrade over time due to wear or staining sustained during medical or surgical procedures. This disposable or consumable feature is conducive to surgical use in relation to sterility concerns as well. A fastening feature may be included to retain the drape in place, e.g., in relation to a trackable object, e.g., an end effector. The contrast elements provide a better line-of-sight, whereby blocking a line-of-sight by the drape is prevented. Alternatively, the contrast elements, e.g., the dishes, are integrated into the drape, whereby the tracking markers are configured to couple with marker tools or the contract elements, and whereby puncturing the drape is punctured, in accordance with some embodiments of the present disclosure. Otherwise, puncturing the drape would break sterility, and require the trackable object to be re-draped as is often a problem in the related art. Such embodiments of the contrast system eliminate such related art problems.

Some embodiments of the present disclosure use tracking markers comprising, spherical tracking markers, in conjunction with contrast elements, comprising a parabolic dish configuration, wherein the combination of the tracking markers and the contrast elements are configured to either interact with a drape or to integrally form with the drape. The contrast elements of the present disclosure are also adaptable for use in relation to a 3D marker tree, comprising tracking markers, such as conical markers or spherical markers, for facilitating visibility in different orientations, e.g., in a plurality of planes, whereby line-of-sight, tracking, and navigation challenges in the related art are addressable. The combination of the tracking markers and the contrast elements are also configured to couple with an end effector.

Figure 2A:
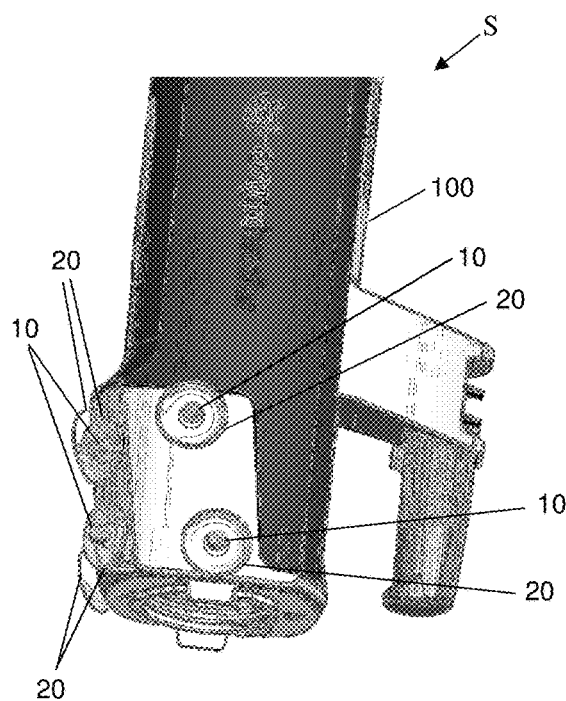
FIG. 2A is a diagram illustrating a perspective view of a plurality of tracking markers, as observed by a tracking camera of a tracking system, wherein a correct number and correct shapes of tracking markers are observed, the tracking of which is enhanced by a contrast system, in accordance with embodiments of the present disclosure.
Figure 1B:
FIG. 1B is a diagram illustrating a perceived image of a plurality of tracking markers, as observed by a tracking camera of a tracking system, wherein an erroneous excess number and erroneous shapes of the tracking markers are observed, as shown in FIG. 1A, in accordance with the related art.
Figure 2B:
FIG. 2B is a diagram illustrating an image of a plurality of tracking markers, as observed by a tracking camera of a tracking system, wherein a correct number and correct shapes of tracking markers are observed, the tracking of which is enhanced by a contrast system, as shown in FIG. 2A, in accordance with embodiments of the present disclosure.
Figure 2C:
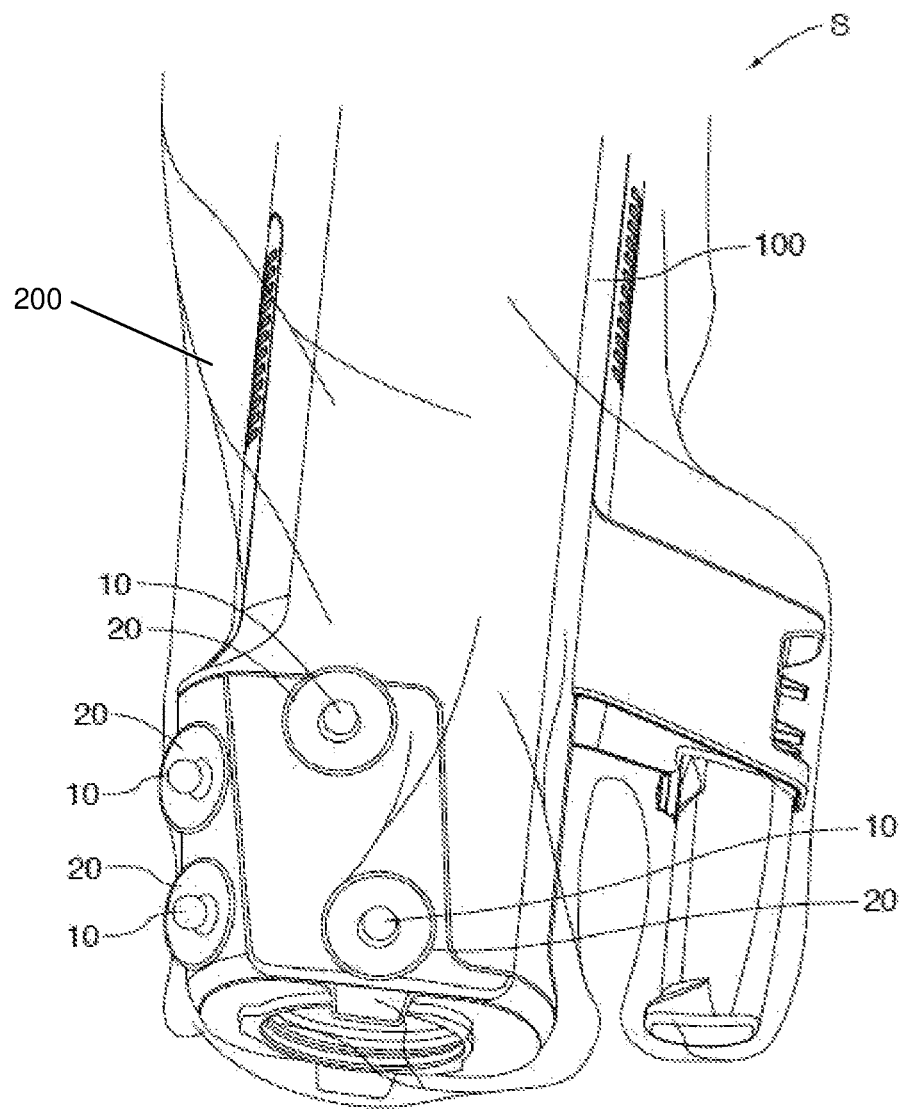
FIG. 2C is a diagram illustrating a perspective view of a contrast system interacting with, or integrated with, a background object, being coupled with a trackable object, in accordance with an embodiment of the present disclosure.
Figure 5:
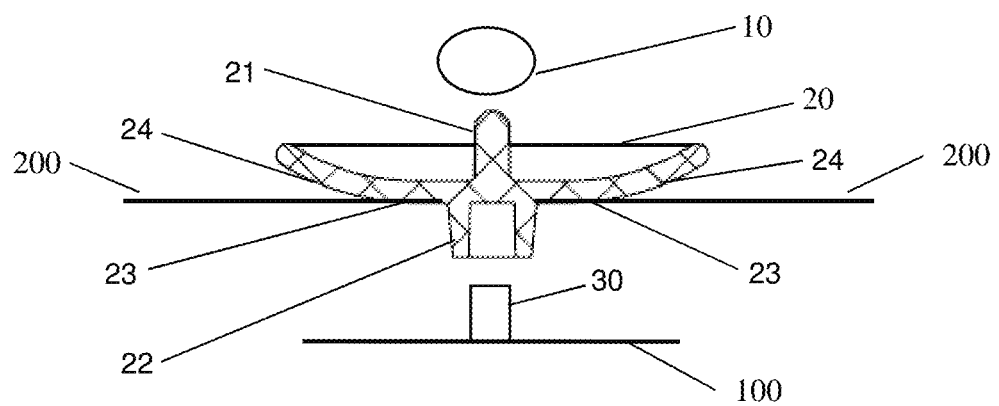
FIG. 5 is a diagram illustrating a cross-sectional view of a contrast element, taken along a cross-section, as included in a contrast system for improving optical detection during a medical procedure, as shown in FIG. 3, in accordance with an embodiment of the present disclosure.

Referring to FIGS. 2A through 2C, this diagram illustrates, in a perspective view, a plurality of tracking markers 10, as observed by a tracking camera (not shown) of a tracking system (not shown), wherein a correct number and shape of the tracking markers 10 are observed, the observational accuracy being enhanced by way of a contrast system S, in accordance with embodiments of the present disclosure. The contrast system S improves optical detection during a medical procedure, in accordance with an embodiment of the present disclosure. The contrast system S comprises: at least one tracking marker 10, each at least one tracking marker 10 comprising a tracking marker coupling feature (not shown); and at least one contrast element 20, each at least one contrast element 20 comprising a contrast element coupling feature 21 and an optically non-reflective feature (not shown), the contrast element coupling feature 21 configured to complement the tracking marker coupling feature (not shown), each at least one contrast element 20 configured to respectively accommodate, by backing, each at least one tracking marker 10, and each at least one contrast element 20 configured to respectively facilitate coupling each at least one tracking marker 10 with at least one trackable object 100, such as an end effector, through at least one background object 200, such as a surgical drape, via at least one of a contrast element fastening feature and a trackable object fastening feature, as shown in FIG. 5, whereby optical contrast between that least one tracking marker 10 and the at least one background object 200 is enhanceable, false detection of the at least one tracking marker 10 is minimizable, and optical detection of the at least one tracking marker 10 is improvable, in accordance with an embodiment of the present disclosure. In alternative embodiments of the contract system S, at least one tracking marker 10 and the at least one contrast element 20 may be integrally formed.

Still referring to FIGS. 2A through 2C, in the system S, one of the following configurations is implemented: (a) the tracking marker coupling feature (not shown) comprises a tracking marker recess (not shown) and the contrast element coupling feature 21 (shown in FIG. 3) comprises a contrast element protrusion configured to complement the tracking marker recess (not shown), and (b) the tracking marker coupling feature 21 comprises a tracking marker protrusion and the contrast element coupling feature 21 comprises contrast element recess (not shown), in accordance with some embodiments of the present disclosure. In either configuration, the tracking marker coupling feature (not shown) and the contrast element coupling feature 21, together, provide an interference fit. In the system S, at least one of the at least one contrast element 20 and the at least one tracking marker 10 is disposable or consumable.

Still referring to FIGS. 2A through 2C, the system S further comprises the at least one background object 200, in accordance with an embodiment of the present disclosure. The at least one background object 200 comprises at least one of a drape, and a surgical drape. The at least one background object 200 also comprises a through-hole for facilitating coupling of the at least one contrast element 20 to at least one trackable object 100 by way of the trackable object fastening feature 30. Alternatively, through-holes are formed in a background object, e.g., a drape, wherein the contrast elements, e.g., the dish, are inserted and integrally coupled with the background object, e.g., the drape. In such embodiment, the through-holes are sealed by the contrast elements, whereby sterility of the surgical environment is maintained.

Still referring to FIGS. 2A through 2C, in the system S, the at least one tracking marker 10 comprises at least one feature of a passive marking feature, a spherical shape, a reflective feature, a retro-reflective feature, and an infrared retro-reflective feature, in accordance with some embodiments of the present disclosure. The at least one tracking marker 10 comprises a plurality of tracking markers 10, wherein the plurality of tracking markers 10 is arranged in a pattern, and whereby optical distortion is minimizable. In the system S, a plurality of tracking markers 10, as observed by a tracking camera (not shown) of a tracking system (not shown) in an image having marker images 10' (FIG. 2B), wherein a correct number and shape of the tracking markers 10 is observed, in accordance with embodiments of the present disclosure.

Figure 3:
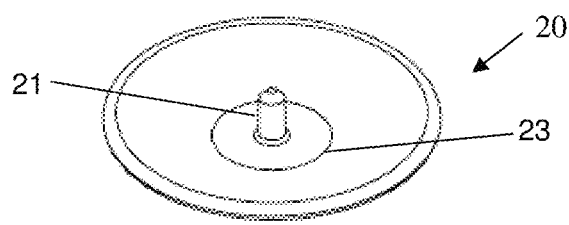
FIG. 3 is a diagram illustrating a perspective view of a contrast element, as included in a contrast system for improving optical detection during a medical procedure, in accordance with an embodiment of the present disclosure.

Referring to FIG. 3, this diagram illustrates, in a perspective view, a contrast element 20 of a contrast system S for improving optical detection during a medical procedure, in accordance with an embodiment of the present disclosure. The at least one contrast element 20 further comprises at least one of a concave shape, a parabolic shape, a disk shape, and a dish shape. Also, the at least one contrast element 20 further comprises at least one of a polymeric material, an optically absorbent material, and a composite material. The optically absorbent material is configured to absorb light in at least one wavelength spectrum of a visible spectrum, an ultraviolet spectrum, an ultraviolet-visible spectrum, an infrared spectrum, and a near-infrared spectrum. The at least one contrast element 20, in at least one of a concave shape, a parabolic shape, a disk shape, and a dish shape, facilitates minimizing false detection of the at least one tracking marker 10 by blocking a sight line thereto.

Figure 4:
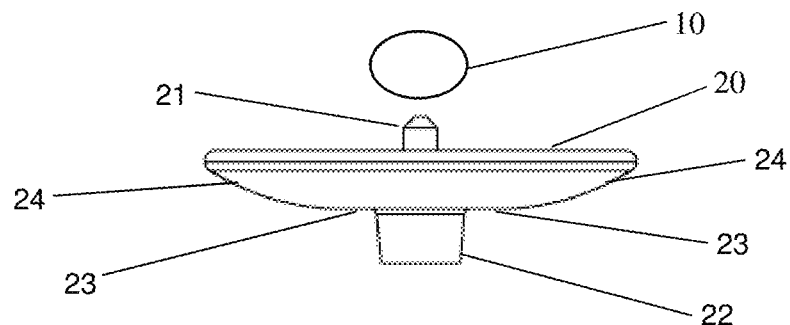
FIG. 4 is a diagram illustrating a side view of a contrast element, as included in a contrast system for improving optical detection during a medical procedure, as shown in FIG. 3, in accordance with an embodiment of the present disclosure.

Referring to FIG. 4, this diagram illustrates, in a side view, of a contrast element 20, as shown in FIG. 3, of a contrast system S, having a cross section A-A, as shown in FIG. 5, for improving optical detection during a medical procedure, in accordance with an embodiment of the present disclosure. The contrast element 20 further comprises a receiving feature 22 configured to accommodate the fastening feature 30 (FIG. 5). The contrast element 20 further comprises a curved portion 24 as well as a flat portion 23 configured to accommodate a lower surface of the tracking marker 10. The tracking marker 10 is disposed at the tip or distal end of the contrast element coupling feature 21. At least one of the contrast element coupling feature 21 and the receiving feature 22 is integrally formed with the flat portion 23, in accordance with some embodiments of the present disclosure. The flat portion 23 comprises a generally annular flat surface and is disposed around the contrast element coupling feature 21, in accordance with an embodiment of the present disclosure. The flat portion 23 facilitates either coupling or integral forming of the contrast element 20 with the background object 200, e.g., the drape.

Referring to FIG. 5, this diagram illustrates, in a cross-sectional view, taken along a cross-section A-A (FIG. 4), of a contrast element 20, as shown in FIG. 3, of a contrast system S for improving optical detection during a medical procedure, in accordance with an embodiment of the present disclosure. The contrast element 20 may further comprise a contrast element fastening feature (not shown). The contrast element fastening feature (not shown) is coupled with each at least one contrast element 20 and comprises at least one of a post, an adhesive, an adhesive tape, an interference fitting, a hook-and-loop fastener, and a magnet, in accordance with some embodiments of the present disclosure. The post is configured to provide an interference fit in relation to complementary recess (not shown) of the at least one trackable object 100, such as an end effector. Alternatively, the trackable object 100 comprises a trackable object fastening feature 101, wherein the receiving feature 22 of the contrast element 20 is configured to accept the trackable object fastening feature 101. The trackable object fastening feature 101 is coupled with or integrally formed with the trackable object 100 and may also comprise at least one of a post, an adhesive, an adhesive tape, an interference fitting, a hook-and-loop fastener, and magnet, in accordance with some embodiments of the present disclosure.

Referring back to FIGS. 4 and 5, in a system S, the contrast element 20 comprises a diameter of approximately 39.85 mm. The contrast element coupling feature 21 comprises a proximal end diameter of approximately 3.09 mm and a height of approximately 6.5 mm. The coupling feature 21 may comprises a frusto-conical configuration and a distal end diameter of approximately 1.06 mm. The receiving feature 22 comprises a height of approximately 5 mm and an inner diameter of approximately 4.13 mm for accommodating a fastening feature 30 comprising an outer diameter of approximately 4.3 mm, whereby an interference-fit is effected. The curved portion 24 and the seat portion 23, together, comprise a height of approximately 7.5 mm.

Figure 6:
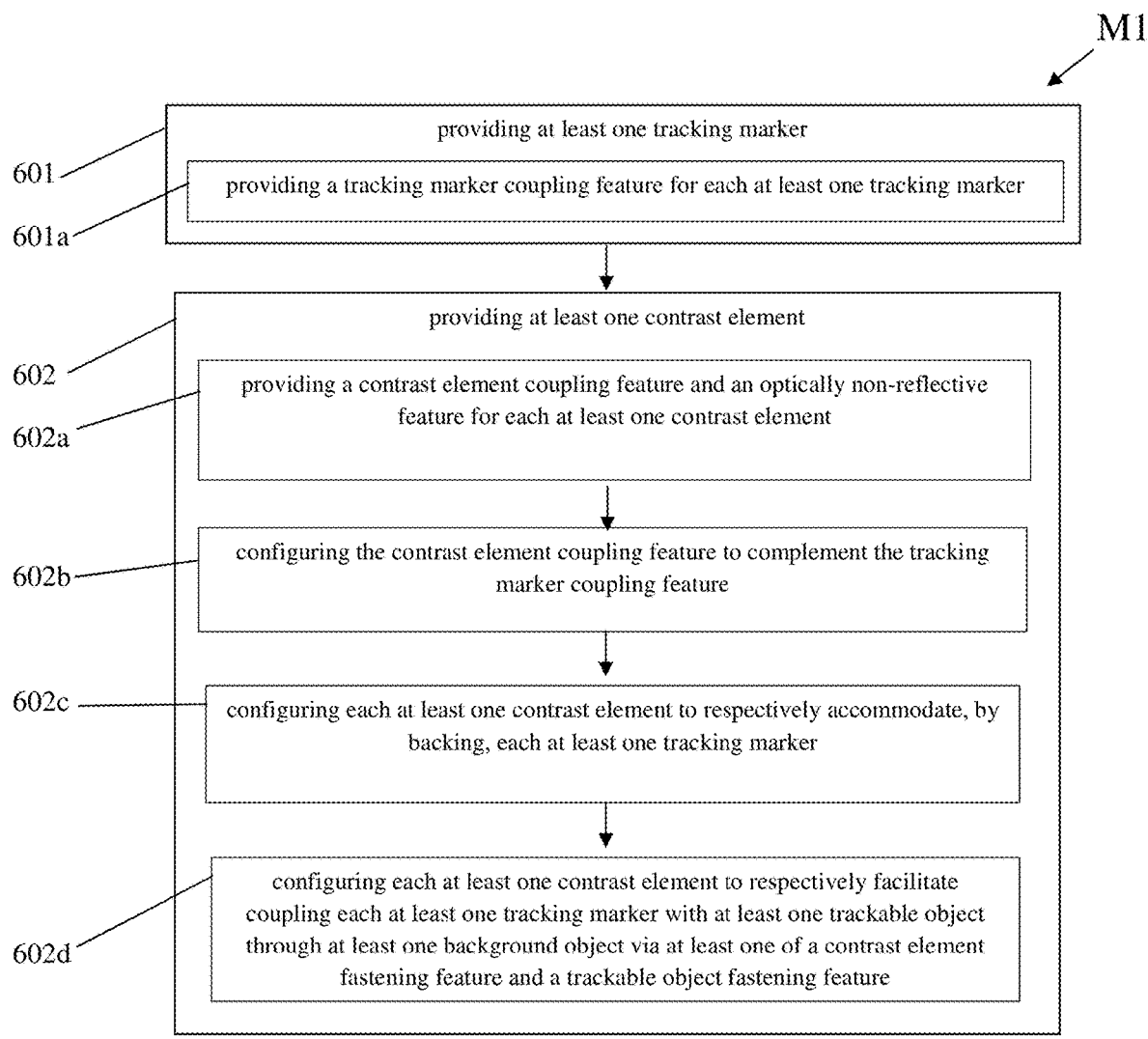
FIG. 6 is a flow diagram illustrating a method of fabricating a contrast system for improving optical detection during a medical procedure, in accordance with an embodiment of the present disclosure.

Referring to FIG. 6, this flow diagram illustrates a method M1 of fabricating a contrast system S for improving optical detection during a medical procedure, in accordance with an embodiment of the present disclosure. The method M1 comprises: providing at least one tracking marker 10, as indicated by block 601, providing the at least one tracking marker 10 comprising providing a tracking marker coupling feature (not shown) for each at least one tracking marker 10, as indicated by block 601a; and providing at least one contrast element 20, as indicated by block 602, providing the at least one contrast element 20 comprising providing a contrast element coupling feature 21 and an optically non-reflective feature (not shown) for each at least one contrast element 20, as indicated by block 602a, providing the contrast element coupling feature 21 comprising configuring the contrast element coupling feature 21 to complement the tracking marker coupling feature (not shown), as indicated by block 602b, and providing the at least one contrast element 20 comprising: configuring each at least one contrast element 20 to respectively accommodate, by backing, each at least one tracking marker 10, as indicated by block 602c, and configuring each at least one contrast element 20 to respectively facilitate coupling each at least one tracking marker 10 with at least one trackable object 100 through at least one background object 200 via at least one of a contrast element fastening feature (not shown) a trackable object fastening feature 101, as indicated by block 602d, whereby optical contrast between that least one tracking marker 10 and the at least one background object 200 is enhanceable, false detection of the at least one tracking marker 10 is minimizable, and optical detection of the at least one tracking marker 10 is improvable. Further, optical contrast between the at least one tracking marker 10 and any object, such as the trackable object 100, that is disposed behind the at least one contrast element 20.

Still referring to FIG. 6, in the method M1, providing the at least one tracking marker 10 comprises one of: providing the tracking marker coupling feature (not shown) comprises providing a tracking marker recess (not shown) and providing the contrast element coupling feature 21 comprises providing a contrast element protrusion configured to complement the tracking marker recess (not shown), and providing the tracking marker coupling feature (not shown) comprises providing a tracking marker protrusion and providing the contrast element coupling feature 21 comprises providing a contrast element recess (not shown), whereby an interference-fit is provided. Alternatively, the at least one contrast element 20 is configured to capture the at least one tracking marker 10 in any other manner, such as by a threaded feature, a slidable feature, and a sliding lock. Also, alternatively, the at least one contrast element 20 may be integrally formed with the at least one tracking marker 10.

Still referring to FIG. 6, the method M1 further comprises providing the at least one background object 200, in accordance with an embodiment of the present disclosure. Providing the at least one background object 200 comprises providing at least one of a drape, and a surgical drape. Providing the at least one background object 200 comprises providing a through-hole (not shown) for facilitating coupling of the at least one contrast element 20 to at least one trackable object 100 by way of a contrast element fastening feature (not shown). Alternatively, providing the at least one background object 200 comprises integrally forming the at least one background object 200 with at least one of the at least one contrast element 20 and the at least one tracking marker 10. In yet another alternative embodiment, providing the at least one background object 200 comprises providing a trackable object fastening feature 101.

Still referring to FIG. 6, in the method M1, providing the at least one tracking marker 10 comprises providing at least one feature of a passive marking feature, a spherical shape, a reflective feature, a retro-reflective feature, and an infrared retro-reflective feature, in accordance with some embodiments of the present disclosure. Providing the at least one tracking marker 10 comprises providing a plurality of tracking markers 10; and providing the plurality of tracking markers 10 comprises arranging the plurality of tracking markers 10 in a pattern, whereby optical distortion is minimizable.

Still referring to FIG. 6, in the method M1, providing the at least one contrast element 20 further comprises providing at least one of a concave shape, a parabolic shape, a disk shape, and a dish shape, in accordance with some embodiments of the present disclosure. Providing the at least one contrast element 20 further comprises providing at least one of a polymeric material, an optically absorbent material, and a composite material. Providing the optically absorbent material comprises configuring the optically absorbent material to absorb light in at least one wavelength spectrum of a visible spectrum, an ultraviolet spectrum, an ultraviolet-visible spectrum, an infrared spectrum, and a near-infrared spectrum.

Still referring to FIG. 6, in the method M1, providing the at least one contrast element 20, in at least one of a concave shape, a parabolic shape, a disk shape, and a dish shape, facilitates minimizing false detection of the at least one tracking marker 10 by blocking a sight line thereto, in accordance with some embodiment of the present disclosure. At least one of providing the at least one contrast element 20 and providing the at least one tracking marker 10 comprises providing the at least one contrast element 20 and providing the at least one tracking marker 10 as being disposable or consumable.

Still referring to FIG. 6, in the method M1, providing the fastening feature 30 comprises providing at least one of a post, an adhesive, an adhesive tape, an interference fitting, and a hook-and-loop fastener, in accordance with some embodiments of the present disclosure. Providing the post comprises configuring the post to provide an interference fit in relation to complementary recess (not shown) of the at least one trackable object 100.

Figure 7:
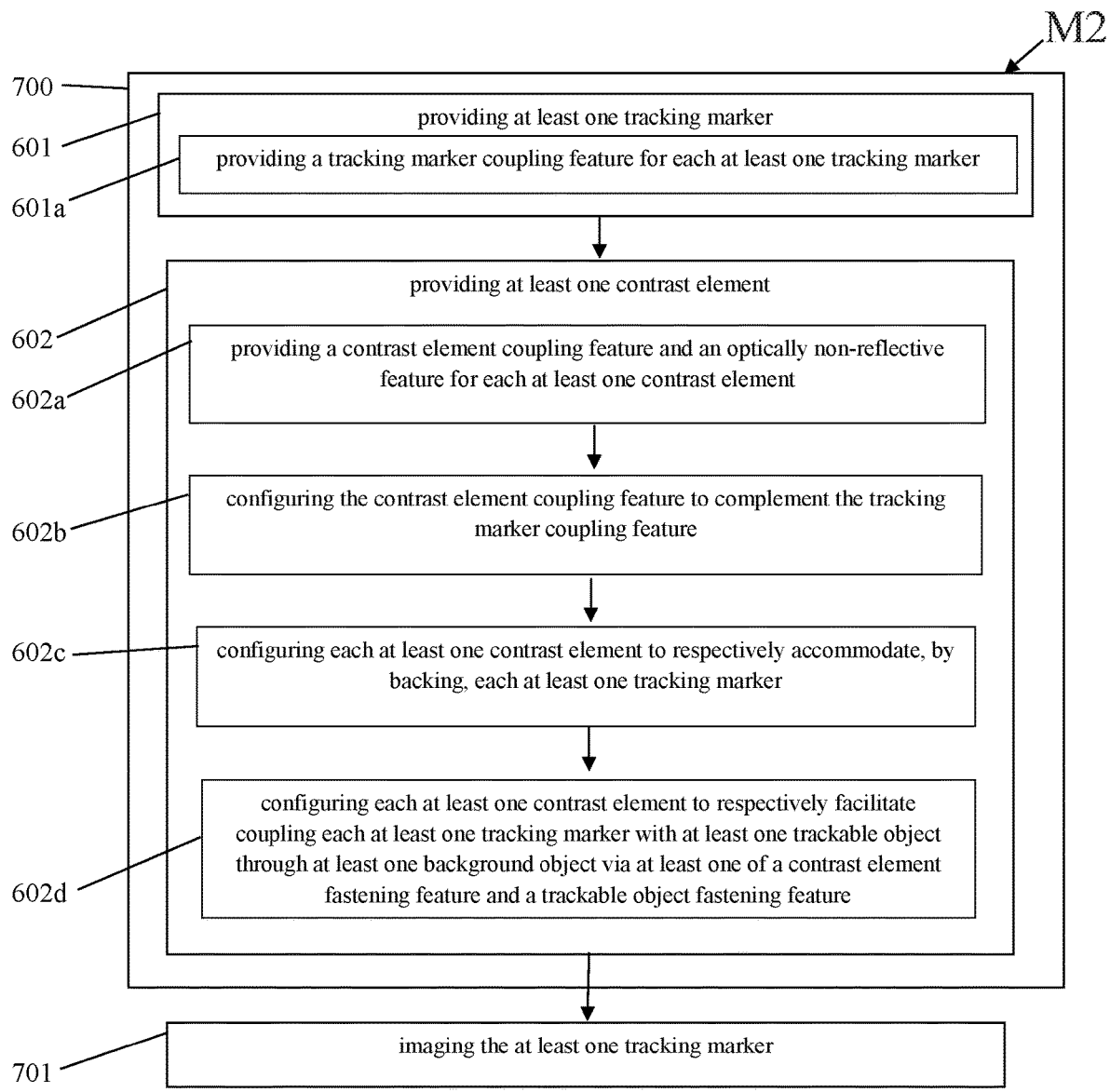
FIG. 7 is a flow diagram illustrating a method of improving optical detection during a medical procedure by way of a contrast system, in accordance with an embodiment of the present disclosure.

Referring to FIG. 7, this flow diagram illustrates a method M2 of improving optical detection during a medical procedure by way of a contrast system S, in accordance with an embodiment of the present disclosure. The method M2 comprises: providing a contrast system S, as indicated by block 700, providing the contrast system S comprising: providing at least one tracking marker 10, as indicated by block 601, providing the at least one tracking marker 10 comprising providing a tracking marker coupling feature (not shown) for each at least one tracking marker 10, as indicated by block 601a; and providing at least one contrast element 20, as indicated by block 602, providing the at least one contrast element 20 comprising providing a contrast element coupling feature 21 and an optically non-reflective feature (not shown) for each at least one contrast element 20, as indicated by block 602a, providing the contrast element coupling feature 21 comprising configuring the contrast element coupling feature 21 to complement the tracking marker coupling feature (not shown), as indicated by block 602b, and providing the at least one contrast element 20 comprising: configuring each at least one contrast element 20 to respectively accommodate, by backing, each at least one tracking marker 10, as indicated by block 602c, and configuring each at least one contrast element 20 to respectively facilitate coupling each at least one tracking marker 10 with at least one trackable object 100 through at least one background object 200 via at least one of a contrast element fastening feature (not shown) a trackable object fastening feature 101, as indicated by block 602d, whereby optical contrast between that least one tracking marker 10 and the at least one background object 200 is enhanceable, false detection of the at least one tracking marker 10 is minimizable, and optical detection of the at least one tracking marker 10 is improvable; and imaging the at least one tracking marker 10, as indicated by block 701, thereby enhancing optical contrast between that least one tracking marker 10 and the at least one background object 200, minimizing false detection of the at least one tracking marker 10, and improving optical detection of the at least one tracking marker 10.

At least some aspects disclosed are embodied, at least in part, in software. That is, some disclosed techniques and methods are carried out in a computer system or other data processing system in response to its processor, such as a microprocessor, executing sequences of instructions contained in a memory, such as ROM, volatile RAM, non-volatile memory, cache or a remote storage device.

A computer readable storage medium is used to store software and data which when executed by a data processing system causes the system to perform various methods or techniques of the present disclosure. The executable software and data is stored in various places including for example ROM, volatile RAM, non-volatile memory and/or cache. Portions of this software and/or data are stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium is the internet cloud, or a computer readable storage medium such as a disc.

Furthermore, at least some of the methods described herein are capable of being distributed in a computer program product comprising a computer readable medium that bears computer usable instructions for execution by one or more processors, to perform aspects of the methods described. The medium is provided in various forms such as, but not limited to, one or more diskettes, compact disks, tapes, chips, universal server bus (USB) keys, external hard drives, wire-line transmissions, satellite transmissions, internet transmissions or downloads, magnetic and electronic storage media, digital and analog signals, and the like. The computer usable instructions may also be in various forms, including compiled and non-compiled code.

At least some of the elements of the systems described herein are implemented by software, or a combination of software and hardware. Elements of the system that are implemented via software are written in a high-level programming language such as object-oriented programming or a scripting language. Accordingly, the program code is written in C, C++, J++, or any other suitable programming language and may comprise functions, modules or classes, as is known to those skilled in computer programming. At least some of the elements of the system that are implemented via software are written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner for performing at least one of the methods described herein.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, any particular order to steps or stages of methods or processes described in this disclosure is not intended or implied. In many cases the order of process steps is varied without changing the purpose, effect, or import of the methods described.

Information as herein shown and described in detail is fully capable of attaining the above-described embodiments of the present disclosure and the presently preferred embodiment, if any, of the present disclosure, and is, thus, representative of the subject matter which is broadly contemplated by the present disclosure. The scope of the present disclosure fully encompasses other embodiments and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a device, an apparatus, a system, or a method to address each, and every, problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail is made, without departing from the spirit and scope of the present disclosure, as set forth in the appended claims, as is apparent, or may become apparent, to those of ordinary skill in the art, are also encompassed by the present disclosure.

INDUSTRIAL APPLICABILITY

Generally, the present disclosure industrially applies to tracking marker systems and methods. More particularly, the present disclosure industrially applies to passive tracking marker systems and methods. Even more particularly, the present disclosure industrially applies to enhancing passive tracking marker systems and methods.

What is claimed:

1. A contrast system, the system comprising:
at least one tracking marker, each at least one tracking marker comprising a tracking marker coupling feature; and
at least one contrast element, each at least one contrast element comprising a contrast element coupling feature and an optically non-reflective feature,
the contrast element coupling feature configured to complement the tracking marker coupling feature,
each at least one contrast element configured to respectively accommodate, by backing, each at least one tracking marker, and each at least one contrast element configured to respectively facilitate coupling each at least one tracking marker with at least one trackable object through at least one background object via at least one of a contrast element fastening feature and a trackable object fastening feature, and the at least one contrast element further comprising at least one of a concave shape, a parabolic shape, and a dish shape, and whereby at least one of optical contrast and imaging in relation to the at least one tracking marker and the at least one background object is enhanced, false detection of the at least one tracking marker is minimized, and optical detection of the at least one tracking marker is improved.

2. The system of claim 1, wherein one of:

the tracking marker coupling feature comprises a tracking marker recess and the contrast element coupling feature comprises a contrast element protrusion configured to complement the tracking marker recess; and the tracking marker coupling feature comprises a tracking marker protrusion and the contrast element coupling feature comprises a contrast element marker recess;

whereby a tracking-marker-to-contrast-element coupling, comprising at least one of an interference fit and a capturing mechanism, is provided.

3. The system of claim 1, further comprising the at least one background object, wherein the at least one background object comprises at least one of a drape, and a surgical drape;

wherein the at least one background object is one of fastened to the at least one contrast element and integrally formed with the at least one contrast element.

4. The system of claim 1, wherein the at least one tracking marker comprises at least one feature of a passive marking feature, a spherical shape, a reflective feature, a retro-reflective feature, and an infrared retro-reflective feature.

5. The system of claim 1, wherein the at least one tracking marker comprises a plurality of tracking markers; wherein the plurality of tracking markers is arranged in a pattern, and whereby optical distortion is minimized.

6. The system of claim 1, wherein the at least one contrast element further comprises a disk shape, and wherein the at least one contrast element further comprises at least one of a polymeric material, an optically absorbent material, and a composite material.

7. The system of claim 6, wherein the optically absorbent material is configured to absorb light in at least one wavelength spectrum of a visible spectrum, an ultraviolet spectrum, an ultraviolet-visible spectrum, an infrared spectrum, and a near-infrared spectrum.

8. The system of claim 6, wherein the at least one contrast element, in at least one of a concave shape, a parabolic shape, a disk shape, and a dish shape, facilitates minimizing false detection of the at least one tracking marker by blocking a sight line thereto.

9. The system of claim 1, wherein at least one of the at least one contrast element and the at least one tracking marker is at least one of disposable and consumable.

10. The system of claim 1, wherein the fastening feature comprises at least one of a post, an adhesive, an adhesive tape, an interference fitting, a hook-and-loop fastener, and a magnetic feature; and wherein the post is configured to provide an interference fit in relation to complementary recess of the at least one trackable object.

11. A method of fabricating a contrast system, the method comprising:

providing at least one tracking marker, providing the at least one tracking marker comprising providing a tracking marker coupling feature for each at least one tracking marker; and providing at least one contrast element, providing the at least one contrast element comprising providing a contrast element coupling feature and an optically non-reflective feature for each at least one contrast element, providing the contrast element coupling feature comprising configuring the contrast element coupling feature to complement the tracking marker coupling feature, providing the at least one contrast element comprising: configuring each at least one contrast element to respectively accommodate, by backing, each at least one tracking marker, and configuring each at least one contrast element to respectively facilitate coupling each at least one tracking marker with at least one trackable object through at least one background object via at least one of a contrast element fastening feature and a trackable object fastening feature, and providing the at least one contrast element further comprising providing at least one of a concave shape, a parabolic shape, and a dish shape, whereby at least one of optical contrast and imaging in relation to the at least one tracking marker and the at least one background object is enhanced, false detection of the at least one tracking marker is minimized, and optical detection of the at least one tracking marker is improved.

12. The method of claim 11, wherein one of:

providing the tracking marker coupling feature comprises providing a tracking marker recess and providing the contrast element coupling feature comprises providing a contrast element protrusion configured to complement the tracking marker recess; and providing the tracking marker coupling feature comprises providing a tracking marker protrusion and providing the contrast element coupling feature comprises providing a contrast element recess;

whereby a tracking-marker-to-contrast-element coupling, comprising at least one of an interference fit and a capturing mechanism, is provided.

13. The method of claim 11, further comprising providing the at least one background object, wherein providing the at least one background object comprises providing at least one of a drape, a surgical drape; and wherein providing the at least one background object comprises one of fastening the ate last one background object to the at least one contrast element and integrally forming the at least one background object with the at least one contrast element.

14. The method of claim 11, wherein providing the at least one tracking marker comprises providing at least one feature of a passive marking feature, a spherical shape, a reflective feature, a retro-reflective feature, and an infrared retro-reflective feature.

15. The method of claim 11, wherein providing the at least one tracking marker comprises providing a plurality of tracking markers, and wherein providing the plurality of tracking markers comprises arranging the plurality of tracking markers in a pattern.

16. The method of claim 11,
wherein providing the at least one contrast element further comprises providing a disk shape, and
wherein providing the at least one contrast element further comprises providing at least one of a polymeric material, an optically absorbent material, and a composite material; and
wherein providing the optically absorbent material comprises configuring the optically absorbent material to absorb light in at least one wavelength spectrum of a visible spectrum, an ultraviolet spectrum, an ultraviolet-visible spectrum, an infrared spectrum, and a near-infrared spectrum.

17. The method of claim 16, wherein providing the at least one contrast element, in at least one of a concave shape, a parabolic shape, a disk shape, and a dish shape, facilitates minimizing false detection of the at least one tracking marker by blocking a sight line thereto.

18. The method of claim 11, wherein at least one of providing the at least one contrast element and providing the at least one tracking marker comprises providing the at least one contrast element and providing the at least one tracking marker as being at least one of disposable and consumable.

19. The method of claim 11,
wherein providing the fastening feature comprises providing at least one of a post, an adhesive, an adhesive tape, an interference fitting, a hook-and-loop fastener, and a magnetic feature; and
wherein providing the post comprises configuring the post to provide an interference fit in relation to complementary recess of the at least one trackable object.

20. A contrast system, the system comprising:
at least one background object;
at least one tracking marker, each at least one tracking marker comprising a tracking marker coupling feature; and
at least one contrast element, each at least one contrast element comprising a contrast element coupling feature and an optically non-reflective feature,
the contrast element coupling feature configured to complement the tracking marker coupling feature, each at least one contrast element configured to respectively accommodate, by backing, each at least one tracking marker, and each at least one contrast element configured to respectively facilitate coupling each at least one tracking marker with at least one trackable object through at least one background object via at least one of a contrast element fastening feature and a trackable object fastening feature,
the at least one background object comprising at least one of a drape, and a surgical drape,
the at least one background object fastened to the at least one contrast element and integrally formed with the at least one contrast element,
the at least one tracking marker comprising at least one feature of a passive marking feature, a spherical shape, a reflective feature, a retro-reflective feature, and an infrared retro-reflective feature,
the at least one tracking marker comprising a plurality of tracking markers, the plurality of tracking markers arranged in a pattern,
the at least one contrast element further comprising at least one of a concave shape, a parabolic shape, and a dish shape for facilitating minimizing false detection of the at least one tracking marker by blocking a sight line thereto;
the at least one contrast element further comprises at least one of a polymeric material, an optically absorbent material, and a composite material, the optically absorbent material configured to absorb light in at least one wavelength spectrum of a visible spectrum, an ultraviolet spectrum, an ultraviolet-visible spectrum, an infrared spectrum, and a near-infrared spectrum, and
at least one of the at least one contrast element and the at least one tracking marker being disposable;
whereby at least one of optical contrast and imaging in relation to the at least one tracking marker and the at least one background object is enhanced, false detection of the at least one tracking marker is minimized, and optical detection of the at least one tracking marker is improved.

* * * * *